(12) United States Patent
Magnusson et al.

(10) Patent No.: US 10,114,242 B2
(45) Date of Patent: Oct. 30, 2018

(54) CURVED AUTOMATIC-DARKENING FILTER

(71) Applicant: 3M INNOVATIVE PROPERTIES COMPANY, St. Paul, MN (US)

(72) Inventors: Kristina M. Magnusson, Djurmo (SE); Britton G. Billingsley, St. Paul, MN (US); Kenneth Jarefors, Borlange (SE); Larissa Zuravskaja, Borlange (SE); Joy L. Manske, Menomonie, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/162,242

(22) Filed: May 23, 2016

(65) Prior Publication Data

US 2016/0262467 A1 Sep. 15, 2016

Related U.S. Application Data

(63) Continuation of application No. 13/713,331, filed on Dec. 13, 2012.

(51) Int. Cl.
*G02F 1/1333* (2006.01)
*G02F 1/1341* (2006.01)
(Continued)

(52) U.S. Cl.
CPC ...... *G02F 1/133305* (2013.01); *G02F 1/1333* (2013.01); *G02F 1/1341* (2013.01);
(Continued)

(58) Field of Classification Search
CPC .......... G02F 1/133305; G02F 1/13439; G02F 1/13318; G02F 1/1396; G02F 1/1341
See application file for complete search history.

(56) References Cited

U.S. PATENT DOCUMENTS 4,240,709 A 12/1980 Hörnell
4,385,806 A 5/1983 Fergason
(Continued)

FOREIGN PATENT DOCUMENTS

CN 201757820 3/2011
EP 706674 10/2001
(Continued)

OTHER PUBLICATIONS

Schott, "Flexible Glass Substrates", Chapter 3, Flexible Flat Panel Displays, edited by G. P. Crawford, 2005, John Wiley & Sons, Ltd, 21 pages.
(Continued)

*Primary Examiner* — Dung Nguyen

(57) ABSTRACT

An automatic-darkening filter 10, 10' that comprises a first polarizer 14, a second polarizer 18, a first liquid-crystal cell 16, and a sensor 64. The first polarizer 14 has a first polarization direction, and the second polarizer 18 has a second polarization direction. The liquid crystal cell 16 is disposed between the first and second polarizers 14, 18 and contains first and second optically-transparent, flexible, glass layers 40 and 42 with the liquid crystal layer 48 being located between these layers. The sensor 64 detects incident light and causes a signal to be sent, which causes molecular rotation within the liquid crystal layer. The inventive automatic-darkening filter is beneficial in that overall product weight can be reduced and the view field can be increased.

19 Claims, 3 Drawing Sheets

(51) Int. Cl.

| | | |
|---|---|---|
| *G02F 1/1335* | (2006.01) | |
| *A41D 13/11* | (2006.01) | |
| *G02F 1/139* | (2006.01) | |
| *A61F 9/02* | (2006.01) | |
| *A61F 9/06* | (2006.01) | |
| *G02F 1/133* | (2006.01) | |
| *G02F 1/1347* | (2006.01) | |
| *G02C 7/10* | (2006.01) | |
| *G02F 1/1343* | (2006.01) | |
| *B29C 65/00* | (2006.01) | |
| *B29C 65/48* | (2006.01) | |
| *B32B 38/18* | (2006.01) | |
| *B29C 65/14* | (2006.01) | |
| *B32B 37/15* | (2006.01) | |

(52) U.S. Cl.
CPC ...... *G02F 1/1396* (2013.01); *G02F 1/133528* (2013.01); *A41D 13/1184* (2013.01); *A61F 9/023* (2013.01); *A61F 9/067* (2013.01); *B29C 65/1406* (2013.01); *B29C 65/4845* (2013.01); *B29C 66/301* (2013.01); *B29C 66/81264* (2013.01); *B29C 66/81421* (2013.01); *B29C 66/81471* (2013.01); *B29C 66/836* (2013.01); *B32B 37/153* (2013.01); *B32B 38/1866* (2013.01); *B32B 2551/00* (2013.01); *G02C 7/101* (2013.01); *G02F 1/13318* (2013.01); *G02F 1/13439* (2013.01); *G02F 1/13471* (2013.01); *G02F 2001/1398* (2013.01); *G02F 2201/56* (2013.01)

(56) References Cited

U.S. PATENT DOCUMENTS

| | | |
|---|---|---|
| 4,561,724 A | 12/1985 | Otaki |
| 4,853,973 A | 8/1989 | Boochard |
| 4,875,235 A | 10/1989 | Kuhlman |
| 5,015,086 A | 5/1991 | Okaue |
| 5,113,270 A | 5/1992 | Fergason |
| 5,140,707 A | 8/1992 | Johnson |
| 5,184,156 A | 2/1993 | Black |
| 5,191,468 A | 3/1993 | Mases |
| 5,208,688 A | 5/1993 | Fergason |
| 5,515,186 A | 5/1996 | Fergason |
| 5,533,206 A | 7/1996 | Petrie |
| 5,793,449 A | 8/1998 | Lagerwall |
| 5,825,441 A | 10/1998 | Hörnell |
| 6,097,451 A | 8/2000 | Palmer |
| 6,185,739 B1 | 2/2001 | Verkic |
| 6,262,787 B1 | 7/2001 | Kamoi |
| 6,887,531 B2 | 5/2005 | Hones |
| 6,934,967 B2 | 8/2005 | Miyashita |
| D517,744 S | 3/2006 | Lee |
| D517,745 S | 3/2006 | Lee |
| D518,923 S | 4/2006 | Curran |
| 7,041,520 B1 | 5/2006 | Hwang |
| D523,728 S | 6/2006 | Lee |
| 7,102,602 B2 | 9/2006 | Kim |
| D532,163 S | 11/2006 | Curran |
| 7,197,774 B2 | 4/2007 | Curran |
| 7,477,330 B2 | 1/2009 | Magnusson |
| 7,735,338 B2 | 1/2010 | Mueller |
| 7,865,968 B2 | 1/2011 | Lilenthal |
| 7,884,888 B2 | 2/2011 | Magnusson |
| 7,986,394 B2 | 7/2011 | Kamoshida |
| 8,241,751 B2 | 8/2012 | Tomamoto |
| 2001/0017681 A1 | 8/2001 | Hornell |
| 2004/0190106 A1 | 9/2004 | McLear |
| 2006/0098153 A1* | 5/2006 | Slikkerveer ....... G02F 1/133305 349/187 |
| 2006/0101552 A1 | 5/2006 | Lee |
| 2006/0107431 A1 | 5/2006 | Curran |
| 2009/0009710 A1 | 1/2009 | Nirmal |
| 2009/0059126 A1 | 3/2009 | Koganezawa |
| 2009/0079886 A1 | 3/2009 | Magnusson |
| 2009/0161048 A1 | 6/2009 | Satake |
| 2009/0201443 A1 | 8/2009 | Sasaki |
| 2009/0284904 A1* | 11/2009 | Wu .................. G02F 1/133305 361/679.01 |
| 2010/0208190 A1 | 8/2010 | Yoshida |
| 2010/0229286 A1 | 9/2010 | Ahlgren |
| 2010/0265421 A1 | 10/2010 | Sundell |
| 2011/0059296 A1 | 3/2011 | Wada |
| 2011/0068492 A1 | 3/2011 | Chen |
| 2011/0120619 A1 | 5/2011 | Harada |
| 2011/0255039 A1 | 10/2011 | Enomoto |
| 2011/0299025 A1* | 12/2011 | Sahouani ................ A61F 9/067 349/194 |
| 2012/0292488 A1 | 11/2012 | Saadat |
| 2013/0180653 A1 | 7/2013 | Kim et al. |
| 2014/0168546 A1 | 6/2014 | Magnusson |

FOREIGN PATENT DOCUMENTS

| | | |
|---|---|---|
| EP | 1935386 | 6/2008 |
| JP | 4175725 | 6/1992 |
| JP | 7301789 | 11/1995 |
| JP | 2008-112001 | 5/2008 |
| JP | 2009-237278 | 10/2009 |
| JP | 2010-008875 | 1/2010 |
| JP | 2010-014901 | 1/2010 |
| JP | 2010-156784 | 7/2010 |
| WO | WO 1994/27180 | 11/1994 |
| WO | WO 1995/29428 | 11/1995 |
| WO | WO 1997/15255 | 5/1997 |
| WO | WO 2004/053586 | 6/2004 |
| WO | WO 2007/047264 | 4/2007 |
| WO | WO 2008/074176 | 6/2008 |
| WO | WO 2010/096310 | 8/2010 |
| WO | WO 2012/044583 | 4/2012 |

OTHER PUBLICATIONS

Tammaro, David A. et al., Substrates for Flexible AM Displays, Corning Incorporated, Mar. 2003.

European Application EP13863000 Extended Search Report dated Jun. 28, 2016.

Yamachi et al., "Low Energy-Cost TFT Technologies using Ultra-Thin Flexible Glass Substrate", Active-Matrix Flat Panel Displays and Devices (AM-FPD), 2012 19th International Workshop, IEEE, Jul. 4, 2012, pp. 213-214.

European Application 17 15 4233 Search Report dated May 16, 2017.

* cited by examiner

CURVED AUTOMATIC-DARKENING FILTER

This application is a continuation of U.S. patent application Ser. No. 13/713,331, filed on Dec. 13, 2012, which is incorporated by reference herein in its entirety.

The present invention pertains to a curved light filter that changes from a light-transmission-state to a dark-transmission-state in response to incident light. The curved switchable filter has at least one liquid-crystal layer disposed between thin, flexible, glass substrates.

BACKGROUND

Automatic darkening filters commonly have a switchable filter that automatically changes from a light-transmission-state to a dark-transmission-state in response to incident light. The switching is generally achieved through use of a photodetector that is located on, or as part of, personal protective equipment. The photodetector recognizes the presence of the incident light-to-be-filtered, and an electronic module generates a control voltage that, when applied to the switchable filter, causes the filter to change from the light-transmission-state to the dark-transmission-state.

Automatic light filters have been designed which contain liquid-crystal cells located between polarizing films. U.S. Pat. No. 4,240,709 to Hörnell describes a switchable filter that has a single-twisted, nematic, liquid-crystal cell sandwiched between a pair of mutually crossed polarizers. The liquid-crystal cells are generally flat, optically-transparent, glass substrates that include transparent electrode and alignment layers. The liquid-crystal molecules orientate themselves in a particular direction when a voltage is applied across the liquid-crystal cell under the control of an electronic module. Many commercially available products use this kind of switchable filter.

The use of an automatic-darkening filter in a protective shield gives significant ergonomic benefits. Previously welders, for example, had to "nod" their welding shield down when they struck the welding arc to ensure that their eyes were protected from the torch light. Automatic welding filters eliminated this action since the welding shield could be continuously placed in the down position. As a result, weld pattern quality has been generally improved because more accurate electrode placement can be achieved. Productivity improvements also have been noted since grinding and rework have been correspondingly reduced.

Existing flat-glass automatic darkening filters can, however, add considerable weight to the final product (such as welding shield), which in turn, can create stress and tension in the user's neck and shoulders. The rectangular configuration of the typical glass sandwich construction also tends to limit the wearer's field of view. Known welding filters have been generally limited to rectangular constructions because of difficulties in scribing and breaking the rigid glass substrates.

GLOSSARY

The terms set forth below will have the meanings as defined:

"Automatic darkening filter" means a device that attenuates light in response to an input from the light itself and without an input from a person;

"Band pass filter" means a device that allows light of a certain range of frequency(s) to pass therethrough but rejects the passage of light of other frequencies;

"Curved" means not following a straight line when viewed in cross-section;

"Deformation" with respect to a glass layer means being able to be bent 5 millimeters (mm) over a cantilevered distance of 50 mm from the fixed point without fracture;

"Electric field" means a region surrounding an electric charge, which region can generate a force that can be exerted upon charged particles or molecules;

"Flexible" means being able to withstand deformation into a curved shape without breaking;

"Glass" means an inorganic amorphous non-crystalline solid material that is capable of transmitting visible light;

"Glass layer" or "glass sheet" means glass that has dimensions that are substantially greater in width and length than in thickness;

"Juxtaposed" means to place side by side but not necessarily in contact with each other;

"Liquid crystal layer" means a layer that has molecules in a liquid phase which molecules have some orientational order with respect to each other and have the ability to align in response to an electric field;

"Low twist" means having a twist angle of less than 90 degrees;

"Nematic molecules" means molecules that exhibit parallel axes in response to an electric field;

"Optically-transparent" means that visible light can pass therethrough sufficiently to see the desired image on the opposing side of the structure;

"Orthogonal" means at right angles thereto;

"Polarize" means to cause light to vibrate in a definite pattern;

"Polarizer" means having the ability to polarize visible light;

"Polarization direction" means an orientation resulting from the polarization of light;

"Rotate" means to change orientation;

"Sensor" means a device that can detect the presence of a defined light source and that can send a signal to another device;

"Signal" means an electrical quantity such as voltage; and

"Twist angle" means an angular difference in orientation between two surfaces.

SUMMARY OF THE INVENTION

The present invention provides a switchable filter that comprises a first polarizer, a second polarizer, and a first liquid-crystal cell. The first polarizer has a first polarization direction, and the second polarizer has a second polarization direction. The second polarization direction may be the same or different from the first polarization direction. The liquid-crystal cell is disposed between the first and second polarizers. The liquid crystal cell contains first and second optically-transparent, flexible, glass layers and has a liquid crystal layer located between the first and second curved, optically-transparent flexible glass layers.

The inventive switchable filter is beneficial in that overall product weight can be reduced relative to known commercially-available products. Reductions in weight are achieved by the, low weight of the flexible glass layers. These flexible layers tend to be thinner than the flat glass substrates that have been used in previous conventional products. Further, the inventive switchable filter can be fashioned to have a non-rectangular shape, which improves the user's view field. The user can be provided with an expanded peripheral range of vision in both the horizontal and vertical dimensions. The switchable filter also may be configured in various shapes, for example, to follow the contours of the wearer's face and to accommodate goggles or eye glasses.

DETAILED DESCRIPTION OF PREFERRED EMBODIMENTS

In the practice of the present invention, flexible glass layers define an enclosed area where liquid-crystal molecules are free to rotate under the influence of an electric field to produce a light-filtering effect. The use of flexible glass layers in the manufacture of a switchable filter enables the components of the switchable filter to be laminated together in curved form. This assembly enables a larger viewing area to be achieved for the same (or even less) weight.

Figure 1:
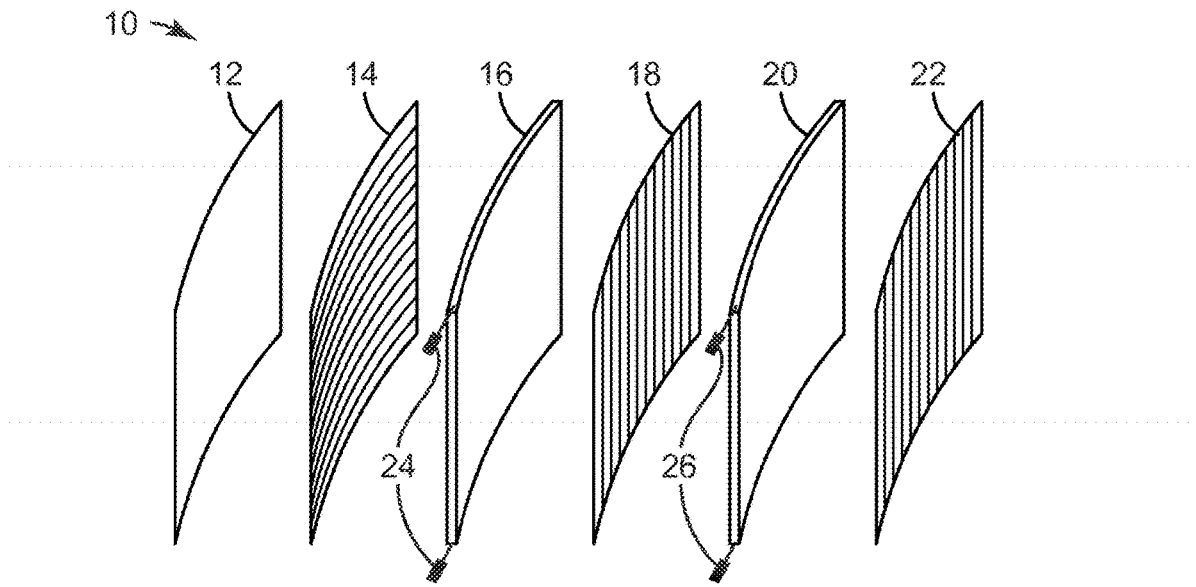
FIG. 1 is an exploded view of a curved, switchable filter 10 according to the present invention.

FIG. 1 shows a curved, switchable, filter 10 where an outermost component of the filter 10 is a band pass filter 12 that serves to attenuate the infra-red (IR) and ultra-violet (UV) wavelength components from a high-intensity incident light. The band pass filter 12 can be an interference filter that reflects the IR radiation and absorbs the UV-A, -B and -C components of the incident light. The band pass filter 12 also may be a combination of separate IR and UV reflecting and/or absorbing filters. The curved, switchable filter 10 also includes a first polarization filter 14, a first optically-rotating liquid-crystal cell 16, and a second polarization filter 18. The polarization filters 14 and 18 have substantially orthogonal polarization directions, where the polarization direction of the first polarization filter 14 is approximately 90° to the polarization direction of the second polarization filter 18 but in a parallel place. The first optically-rotating, liquid-crystal cell 16 may be a twisted, nematic, liquid-crystal cell located between the first and second orthogonally-related polarization filters 14 and 18. In parallel alignment with these components is a second liquid-crystal cell 20, disposed between a pair of polarization filters 18 and 22. The polarization filters 18 and 22 each have substantially parallel polarization directions. The parallel polarization directions enable the cell to be dark when no voltage is applied and light when there is voltage. The default dark-state provides a safety function that notifies the user that the product is turned "off". Each of the liquid crystal cells 16 and 20 are provided with connectors 24 and 26, respectively, by which control voltages can be applied to these cells. The application of a voltage to connectors 24 creates an electric field between the flexible glass layers of the liquid-crystal cell 16. The nematic, liquid-crystal molecules align with the electric field perpendicular to the defining surfaces that enclose the major sides of the cell. This perpendicular alignment, rather than a parallel one, in the excited cell achieves a darkened state. Thus, when a control voltage is applied to the liquid-crystal cell 16, a filter effect is achieved. The liquid-crystal cell controls the polarization of the light, and the light becomes absorbed by the polarizer. The degree of rotation of the nematic molecules may be controlled by varying the control voltage, and thus the corresponding filter effect also may be controlled. The result is that the liquid-crystal cell 16 is in a light transmission state in the absence of an applied voltage and is in a dark transmission state in the presence of the applied voltage. The voltage levels may be different for varying cell designs, depending on the liquid crystal materials used, cell gap geometries, etc. In use, the light transmission state corresponds to any of welding shades 2 to 4, and the dark transmission state, which can be user-selectable, corresponds to any of welding shades 7 to 14. The welding shades have been defined in eye protection standards ANSI 287.1:2010 and 169:2001—see also EN 379: 2003.

Figure 2:
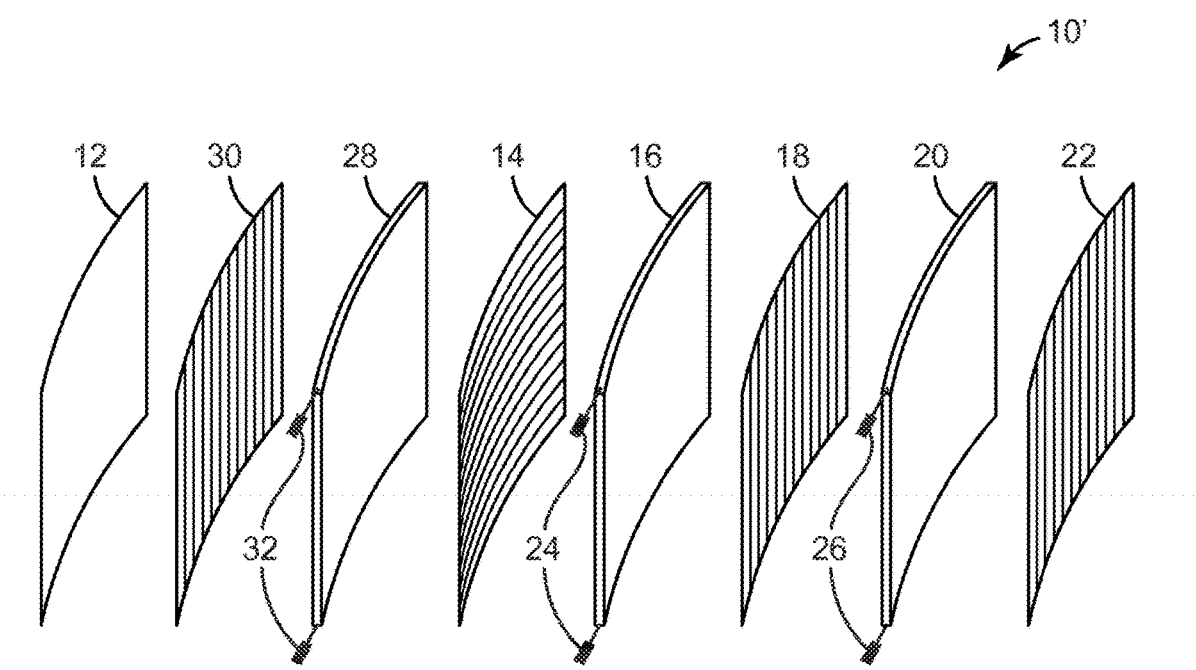
FIG. 2 shows an exploded view of a curved, switchable filter 10' according to the present invention.

FIG. 2 shows an exploded view of a curved, automatic-darkening filter 10' that comprises the liquid-crystal cells 16, 20, and 28. The first liquid-crystal cell 16 is disposed between the first and second polarization filters 14 and 18, the second liquid-crystal cell 20 is disposed between first and third polarization filters 18 and 22, and the third liquid-crystal cell 28 is disposed between polarization filters 30 and 14. The two liquid crystal cells 16 and 28 may be substantially identical, but they are generally rotated about 180° with respect to each other, to give less optical variation for different viewing angles. The application of a voltage to connectors 24 and 32 creates an electric field between transparent conductive electrodes. The nematic, liquid-crystal molecules align with the electric field perpendicular to the surfaces that enclose the molecules to cause the cells to restrict light transmission. The alignment directions of the liquid crystal cells 16 and 28 are arranged substantially parallel to and oriented asymmetrically with respect to one another. The advantages of positioning two substantially-identical, liquid-crystal cells together, such that the face-to-face molecule alignment directions are substantially perpendicular, compensates for an angular dependency of the filtering effect. Variations in shade (improved homogeneity) in the dark state may be achieved using offset polarizers, that is polarizers offset by about 1 to 20 degrees—see U.S. Pat. No. 7,884,888 to Magnusson et al. The offset polarizers may eliminate an uneven shade of the viewing area caused by variations in cell-gap geometry, unwanted birefringence in the adhesive layers of the construction, and different viewing angles.

Figure 3:
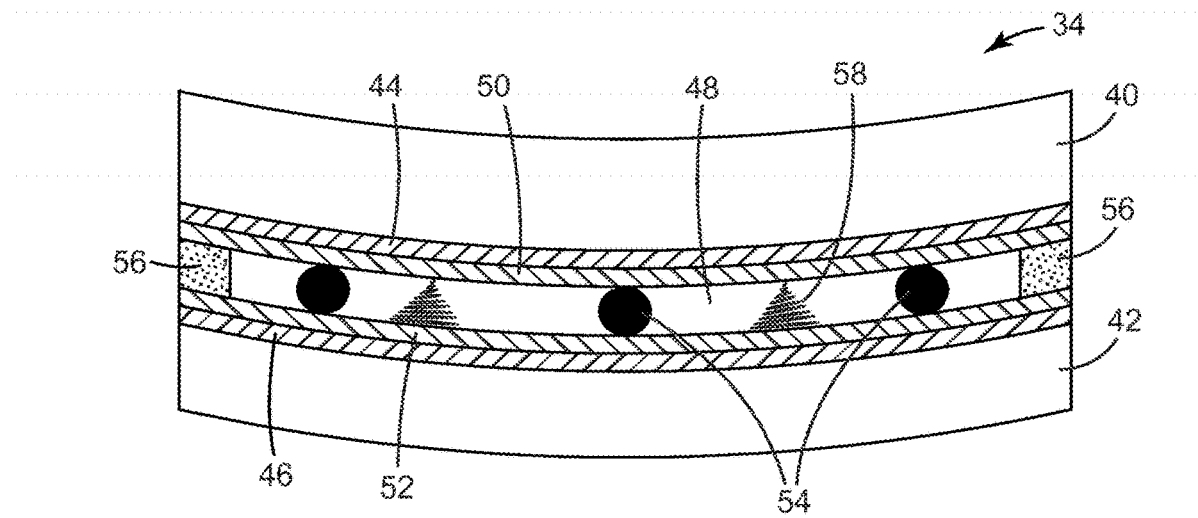
FIG. 3 is a schematic cross-section of a curved liquid-crystal cell 34 that may be used in a switchable filter according to the present invention.

FIG. 3 shows a liquid-crystal cell 34 such as the first, second, and third cells 16, 20, and 28. The laminar construction contains two optically-transparent flexible glass layers 40 and 42. The present invention can be implemented using a variety of such glass layers. The thickness of each of the layers may be about 10 micrometers (μm) to 200 μm, more typically about 30 to 150 μm, and still more typically about 75 to 125 μm. The flexible glass layers 40 and 42 may be supplied in sheet or roll form. The curved layers 40, 42 typically have a radius of less than infinite curvature, typically about 5 to 30 centimeters (cm), more typically about 7 to 20 cm. The curvature also may exhibit a non-constant radius, for example, it may be parabolic, catenary, epicycloidal, and free form. On the inwardly facing surfaces of the optically-clear glass layers 40 and 42 are transparent conductive electrode layers 44 and 46, respectively, (e.g., indium tin oxide layers). By applying a voltage to the electrodes 44 and 46, an electric field is created across the liquid-crystal layer 48 to shift the orientation of the liquid crystal molecules. Juxtaposed against the electrodes 44 and 46 are alignment layers 50 and 52, respectively, for instance, a polyimide layer that has been treated mechanically, such as by brushing or rubbing, in specific alignment directions. The alignment layers 50 and 52 are spaced apart using equally sized spacers 54, inside the cells. The cell edges can be sealed using an edge adhesive 56, such as Norland 68, available from Norland Products, Cranbury, N.J. Before the cell is completely sealed, the nematic molecules 58 are pumped into the gap 48 between the layers 50 and 52. The alignment layers 50 and 52 force the liquid-crystal nematic molecules 58 to take specific angular positions at the surfaces so that the molecules are twisted through their respective twist angle between these surfaces. The rotational condition of the nematic liquid-crystal 58 permits or blocks light-transmission through the cell. The liquid crystals used may be of the nematic type with a Δn (difference between the refractive index of ordinary and extraordinary light rays) of about 08 to 14 sandwiched between the two optically-clear flexible glass layers 40 and 42. The gap between layers 50 and 52 typically is about 3-5 μm. The optically-transparent flexible glass layers 40 and 42 used in the present invention generally have a substantially-uniform optical transmission, typically greater than 80% in the wavelength range of 380 nanometers (nm) to 750 nm. The glass layer may be formed by an overflow downdraw method to have a thickness as indicated above. The composition of the glass layer may be various glass compositions of silicate glass and the like, such as silica glass and borosilicate glass. A non-alkali glass may include glass that does not substantially contain an alkali component, specifically, glass containing an alkali metal oxide of 1000 parts per million (ppm) or less (preferably, of 500 ppm or less, and more preferably, of 300 ppm or less). The glass layer may have a protective sheet juxtaposed against it. When winding the glass layer, the protective sheet prevents occurrence of the flaws, which is caused by contact of one part of the glass layer with another. The protective sheet absorbs external pressure applied to the glass roll. The thickness of the protective sheet may be from 10 μm to 2000 μm. The protective sheet may be an ionomer film, a polyethylene film, a polypropylene film, a polyvinyl chloride film, a polyvinylidene chloride film, a polyvinyl alcohol film, a polypropylene film, a polyester film, a polycarbonate film, a polystyrene film, a polyacrylonitrile film, an ethylene vinyl acetate copolymer film, an ethylen-evinylalcohol copolymer film, an ethylene-methacrylic acid copolymer film, a nylon film (polyamide film), a polyimide film, cellophane or other buffer materials made of resins. Conductivity may be imparted to the protective sheet by adding a component for imparting the same, such as polyethylene glycol, into the protective sheet. In a case where the protective sheet is made of inserting paper, it is possible to impart the conductivity by adding conductive fiber. Further, it is possible to impart the conductivity also by laminating a conductive layer, such as an indium-tin-oxide (ITO) film, on a surface of the protective sheet. See U.S. Pat. No. 8,241,751 to Tomamoto et al.; see also U.S. Pat. No. 7,735,338 to Mueller et al. and U.S. Patent Application Publication 2011/0059296. An example of a commercially-available flexible glass is Schott D263T glass.

Liquid crystal cells 16, 20, and 28 may be a twisted, nematic, liquid-crystal cell type cell that provides a "fail-safe" intermediate transmission state in the case of electronic module failure. An automatic darkening filter that has low-twist, liquid-crystal, cells is described in U.S. Pat. No. 6,097,451 to Palmer et al.; see also U.S. Pat. No. 5,825,441 to Hörnell et al. The twisted, nematic, liquid-crystal cell may have a twist angle of less than 100 degrees, typically zero or 1 to 99 degrees. The liquid-crystal cell also may have a low twist angle of 1 to 85 degrees. More specifically, the twist angle of a low-twist, liquid-crystal, cell may be about 30 to 70 degrees. A "fail-safe" liquid crystal cell is in many ways similar in design to the low-twist, liquid-crystal, cell, but its operation is different because it is sandwiched between parallel polarizers, as opposed to crossed or orthogonal polarizers. Liquid crystal cell 20 is in a dark transmission state (a nearly optically-opaque state in which the majority of the incident light is blocked) when no voltage is applied to the connectors 26. Liquid crystal cell 20 may become optically transparent when a certain voltage is applied.

Figure 4:
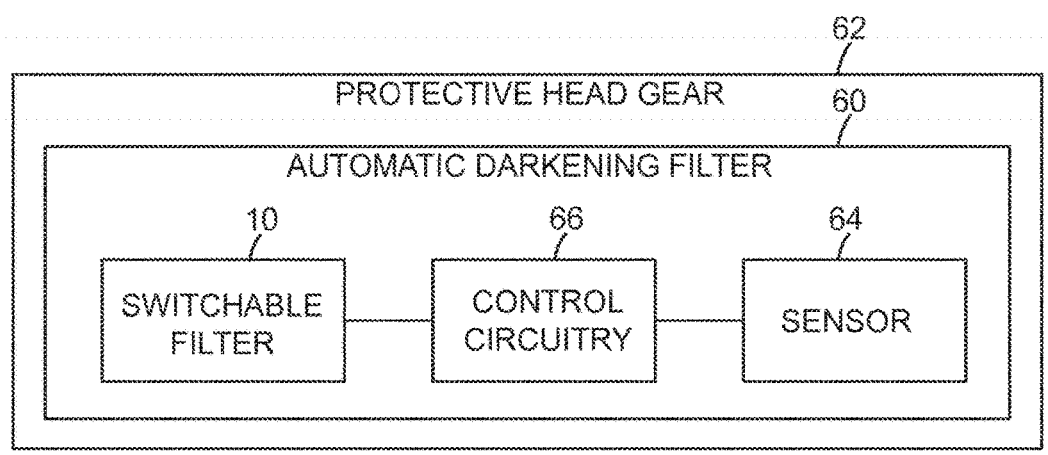
FIG. 4 is a block diagram of the switchable filter 10 (or 10') disposed in an automatic filter darkening apparatus 60 according to the present invention.

FIG. 4 is a block diagram of an automatic darkening filter (ADF) 60. Automatic darkening filter 60 includes a curved switchable filter 10 (or 10') that has offset polarizers of the type described above with respect to FIGS. 1 and 2. Switchable filter 10 is mounted in protective headgear 62 that would be worn by the user during a welding procedure or other situation where protection of the type provided by switchable filter 10 is desired. ADF 60 also includes a sensor 64 for detecting light incident upon the front surface of filter 10, such as a welding arc. The sensor detects incident light and causes a signal to be sent which causes molecular rotation within the liquid crystal layer. The sensor 64 may be provided with a polarizing member that precludes non-normal light from activating the sensor. Such a device prevents light from other welding torches and sensors from reaching the sensor—see U.S. Pat. No. 6,934,967 to Migashita et al. Control circuitry 66 receives signals from the sensor 64 pertaining to the presence or absence of incident light and causes corresponding control voltages to be applied to filter 10, thus controlling the degree of shade provided by filter 10. When the presence of a welding arc or other source of incident light is detected by sensor 64, for example, control circuitry 66 may cause a control voltage to be applied to liquid-crystal cells 16 and 20 (FIGS. 1 and 2) while eliminating the voltage to guest-host cell 28 (FIG. 2). This causes the filter 60 to darken and protect the user from the glare of the incident light. In the absence of a welding arc or other source of incident light, control circuitry 66 may reduce or eliminate the applied voltage to liquid crystal cells 16 and 20, thus causing the filter to become more open to light. This increase in light transmittance enables a welder, for example, to perform a welding operation and also to perform tasks outside the welding area without removing the protective facemask or helmet. In addition, the filter construction described herein results in increased homogeneity in the dark state as seen by the user over a large angular range. The switchable filter 10, sensor 64, and control circuitry 66 are typically supported on a protective headgear as a unit, typically a replaceable unit that is mounted in the shell directly in front of the wearer's eyes when the helmet is worn by the user. The unit may take the form of a rectangular (or other shaped) frame or housing that supports the filter, sensor, and circuitry. Examples of helmet shells may be seen, for example, in U.S. Pat. Nos. 6,185,739, 5,533,206, 5,191,468, 5,140,707, 4,875,235, and 4,853,973. The welding helmets also can have clean air supplied to their interior and thus may include a face seal to separate a breathing zone from the ambient air. An example of such a face seal is shown in U.S. Pat. No. 7,197,774 to Curran et al.; see also U.S. Design Patents D517,744, D517,745, D518,923, D523,728, and D532,163; and U.S. Patent Publication Nos. 2006-0101552, and 2006-0107431.

Figure 5:
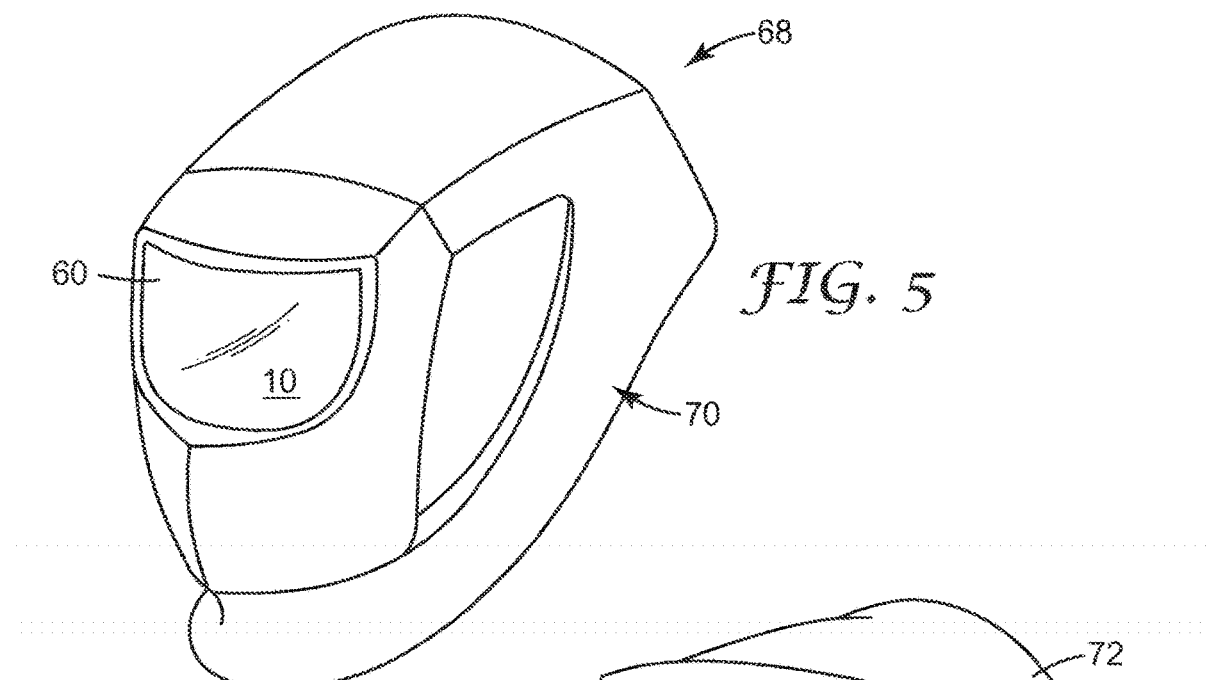
FIG. 5 is a perspective view of welding helmet 68 according to the present invention.

FIG. 5 is a perspective view of a welding helmet 68 that has a helmet body 70 that contains an automatic-darkening filter apparatus 60 mounted within an opening in the helmet body 70. The helmet body 70 may include a crown member that engages the wearer's head when the device 68 is being donned. An example of a suitable crown member is described in U.S. Pat. No. 7,865,968 to Lilenthal et al.; see also, U.S. Patent Application 2010/229286 A1 to Ahlgren et al. The automatic-darkening filter apparatus 60 includes curved automatic darkening filter 10 that is placed in position to intercept electromagnetic radiation (e.g., visible light, UV light, IR, etc.). The automatic-darkening filter 60 may be positioned in the shield body 70 so that it is directly in front of the wearer's eyes when the shield is worn by the user. The automatic-darkening filter 60 may include an electronic control unit 66 (FIG. 5) for receiving and controlling the various signals to the curved automatic welding filter 10 and, more particularly, liquid crystal cells 16, 20 and 28, via connectors 24, 26 and 32, respectively (FIG. 2)—see for example, U.S. Patent Application No. US2010265421 (Sundell). The electronic control unit also may include an input detector that is capable of detecting at least an input from the presence of high intensity light. The detector may be located physically close to some or all of the other components (hardware, etc.) of automatic darkening filter apparatus 60 or may be located physically remote from some or all of these components. The detector can be implemented using various photodetector devices and technologies. Alternatively, an input that indicates the presence of high-intensity light can be generated from an electronic control unit in response to an activation signal generated by, for example, a welding tool or torch—see WO2007/047264 to Garbergs, et al.

Figure 6:
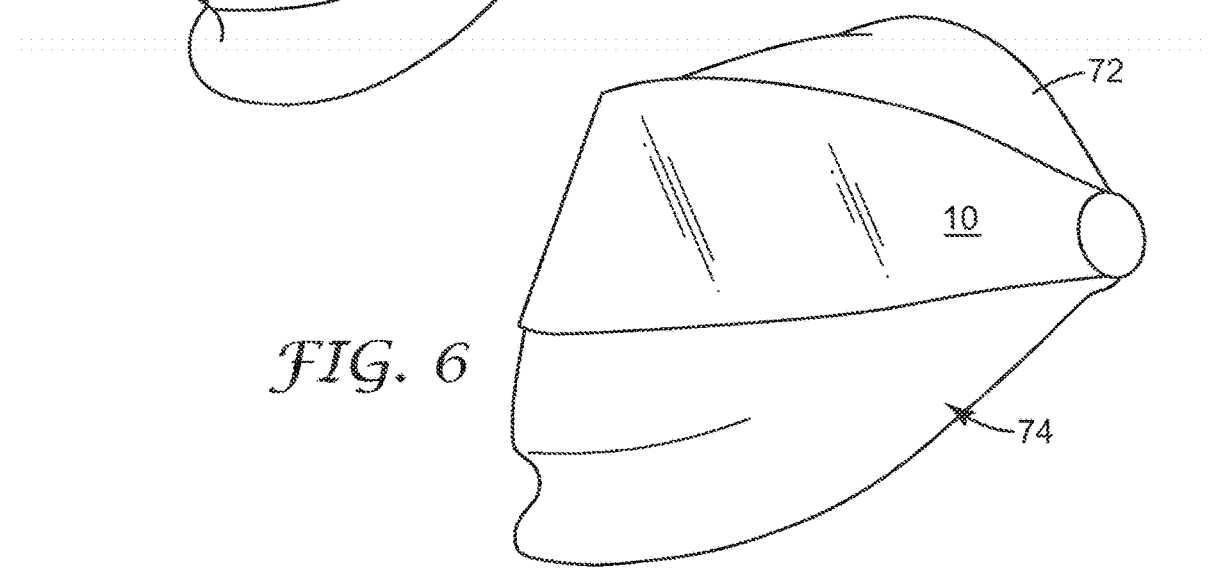
FIG. 6 is a perspective view of protective shield 72 in accordance with the present invention.
Figure 7:
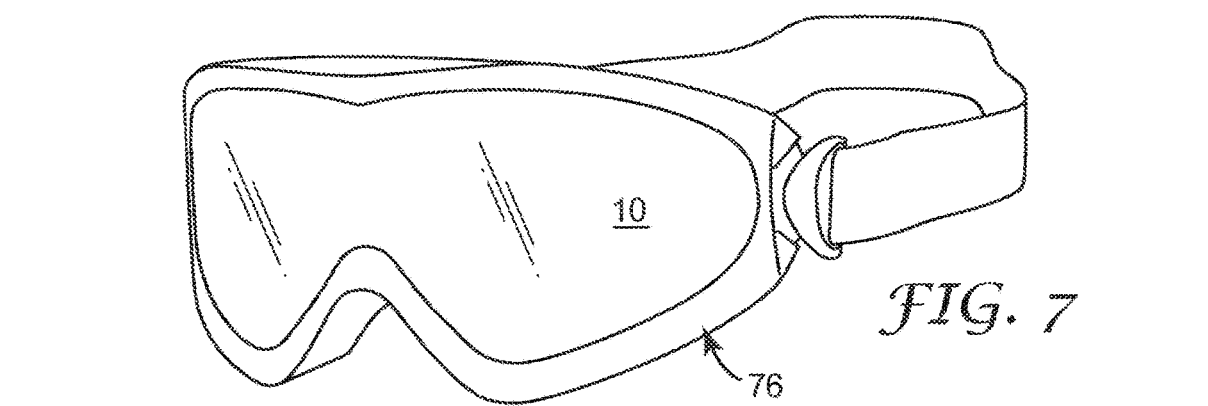
FIG. 7 shows a perspective view of protective goggles 76 in accordance with the present invention.

FIG. 6 is an embodiment of the present invention where the curved, switchable filter 10 of the present invention, is mounted in a suitable face-covering apparatus 72. The switchable filter 10 can be mounted to the face-covering apparatus such that it is rotatable about pivot point 73. Alternatively, the curved automatic welding filter 10 may be mounted in an automatic-darkening filter apparatus disposed in a set of goggles 76 as depicted in FIG. 7.

Switchable filters of the present invention may be curved about one, two, or three axis. Typically a switchable filter used in a welding helmet (FIG. 5) would be curved about one or two axes. The physical properties of the flexible glass layers allow for curved switchable filters to be manufactured which have a radius of curvature of about 5 cm to 20 cm, and a viewing area of about 10 to 600 square centimeters (cm$^2$), more typically 30 cm$^2$ to 250 cm$^2$. Conventional welding filters typically have a viewing area of about 50 to 100 cm$^2$. The present invention may enable switchable filters having a viewing area of at least 100 cm$^2$ to 125 cm$^2$ to be provided.

The automatic darkening filter apparatus of the present invention can be used in connection with industrial operations, for example welding (e.g. arc welding, torch welding, acetylene welding), cutting (e.g. laser cutting, acetylene cutting), brazing, soldering and the like. They also can be used in connection with medical procedures involving high intensity light (e.g. laser surgery, hair removal, tattoo removal, light-curing of dental resins, etc.) and other uses as well. One or more automatic-darkening filter apparatuses may be provided in any other suitable equipment or articles and for other applications. For example, an automatic-darkening filter apparatus may be supplied as part of protective eyewear rather than a full-face coverage helmet. Alternatively, an automatic darkening filter apparatus may be provided in a hand-held device, or in a window or aperture allowing inspection of a room, enclosure, machinery space, etc., in which high intensity light may be present.

EXAMPLE

Liquid Crystal Cell Assembly

A curved liquid crystal cell for an automatic welding filter was made in the following manner.

The starting flexible glass layer was a 0.1 mm thick D263T glass from Schott Glass of Schott Glas Export, GmbH, located at Rheinallee 145, 55120 Mainz, Germany. The glass was sputter deposited with indium tin oxide (ITO). The conductivity of the coated ITO was roughly 100 ohm/square. The ITO glass was coated with a thin layer of polymide polymer. A commercially-available polyimide alignment material was coated onto the glass using a spin coating technique. The dried coating thickness was between 80 nanometers (nm) and 200 nm. The thin polymide layer was aligned by brushing it with using a rotating felt cloth. This brushed polymide, ITO/glass piece was cut into pieces for the top and bottom portion of the liquid crystal cell. A first piece (top) of glass was rotated 90° from the orientation of the second (bottom) piece of glass to provide proper alignment.

The curved, liquid-crystal cell was formed using a metal cylinder that had a radius of approximately 90 millimeters (mm) as the template. The bottom portion of the cell, the ITO glass having the rubbed polyimide coating, was taped to the metal cylinder using 3M Magic Tape™. An edge adhesive (UV curing Norland 68 optical adhesive) was applied to the bottom portion using a syringe and needle. A twisted, nematic, liquid-crystal mixture was combined with 1% by weight of 4 micrometer (µm) ceramic spacer beads. The liquid crystal/spacer bead mixture was placed on the bottom portion of the cell using a pipette. The top portion of the cell was attached to the bottom portion at the leading edge using 3M Removable Tape™. A polyester film, that was attached to the metal cylinder on one end, was used to wrap and curve the top portion of the cell onto the bottom portion. A rubber roll was used to compress the top portion onto the bottom portion. Tension was maintained on the polyester film to keep the components of the cell in close contact. Using a UV light source for 5 minutes, the UV curing edge adhesive was then cured. The completed cell was then removed from the cylinder by removing the polyester film and pieces of tape. Polarizing films were attached to the bottom and top portions using a pressure-sensitive adhesive. The polarizing films were orthogonal to each other and corresponded to the alignment that was rubbed into the polyimide layer. Copper tape, with conductive adhesive, was attached to the ITO on the top portion, and another piece of copper tape with conductive tape was attached to the ITO on the bottom portion. A 10 volt potential was placed across the cell through the copper tape. The cell switched from a light state to a dark state when the voltage was applied. The dimensions of the finished cell were approximately 75 mm wide and 75 mm long (5625 mm$^2$; 56.25 cm$^2$) with a curvature that was slightly less than the 100 mm radius of the original cylinder.

This invention may take on various modifications and alterations without departing from its spirit and scope. Accordingly, this invention is not limited to the above-described but is to be controlled by the limitations set forth in the following claims and any equivalents thereof.

This invention also may be suitably practiced in the absence of any element not specifically disclosed herein.

All patents and patent applications cited above, including those in the Background section, are incorporated by reference into this document in total. To the extent there is a conflict or discrepancy between the disclosure in such incorporated document and the above specification, the above specification will control.

What is claimed is:

1. A method of making a curved switchable filter comprising forming a liquid-crystal cell, wherein forming the liquid-crystal cell comprises:
    forming a first transparent conductive electrode layer on a first optically-transparent flexible glass layer;
    bending the first optically-transparent flexible glass layer such that the first optically-transparent flexible glass layer is curved;
    disposing a liquid-crystal mixture on the transparent conductive electrode layer of the curved first optically-transparent flexible glass layer;
    forming a second transparent conductive electrode layer on a second optically-transparent flexible glass layer; and
    attaching the second optically-transparent flexible glass layer to the curved first optically-transparent flexible glass layer such that the second optically-transparent flexible glass layer is curved, wherein the first transparent conductive electrode layer, the second transparent conductive electrode layer, and the liquid-crystal mixture are disposed between the first optically-transparent flexible glass layer and the second optically-transparent flexible glass layer.

2. The method of claim 1, further comprising disposing a polyimide material on the first transparent conductive electrode layer prior to disposing the liquid-crystal mixture on the transparent conductive electrode layer of the first optically-transparent flexible glass layer.

3. The method of claim 2, further comprising disposing a polyimide material on the second transparent conductive electrode layer prior to attaching the second optically-transparent flexible glass layer to the first optically-transparent flexible glass layer.

4. The method of claim 1, further comprising disposing an edge adhesive on the first optically-transparent flexible glass layer prior to attaching the second optically-transparent flexible glass layer to the first optically-transparent flexible glass layer.

5. The method of claim 4, further comprising curing the edge adhesive after attaching the second optically-transparent flexible glass layer to the first optically-transparent flexible glass layer.

6. The method of claim 1, further comprising disposing the liquid-crystal cell between a first polarizer and a second polarizer, wherein the first polarizer comprises a first polarization direction and the second polarizer comprises a second polarization direction.

7. The method of claim 6, wherein disposing the liquid-crystal cell between the first polarizer and the second polarizer comprises attaching the first polarizer to the first optically-transparent flexible glass layer and attaching the second polarizer to the second optically-transparent flexible glass layer.

8. The method of claim 1, wherein the liquid-crystal mixture comprises liquid crystal molecules and spacer beads.

9. The method of claim 1, wherein each of the first and second optically-transparent flexible glass layers comprises a thickness of 10 to 200 micrometers.

10. The method of claim 9, wherein each of the first and second optically-transparent flexible glass layers comprises a thickness of 30 to 150 micrometers.

11. The method of claim 10, wherein each of the first and second optically-transparent flexible glass layers comprises a thickness of 75 to 125 micrometers.

12. The method of claim 1, wherein each of the first and second optically-transparent flexible glass layers comprises a curvature exhibiting a radius of 5 to 30 centimeters.

13. The method of claim 12, wherein each of the first and second optically-transparent flexible glass layers comprises a curvature exhibiting a radius of 7 to 20 centimeters.

14. The method of claim 12, wherein each of the first and second optically-transparent flexible glass layers comprises a non-constant radius.

15. The method of claim 14, wherein each of the first and second optically-transparent flexible glass layers are parabolic, catenary, epicycloidal, or free form.

16. The method of claim 1, wherein the curved switchable filter comprises a viewing area of at least 100 cm$^2$.

17. The method of claim 1, wherein the curved switchable filter comprises a viewing area of at least 125 cm$^2$.

18. The method of claim 1, wherein bending the first optically-transparent flexible glass layer comprises attaching the first optically-transparent flexible glass layer to a metal cylinder.

19. The method of claim 1, further comprising forming an automatic darkening filter, wherein forming the automatic darkening filter comprises:
    attaching control circuitry to the curved switchable filter; and
    connecting a sensor to the control circuitry.

* * * * *

UNITED STATES PATENT AND TRADEMARK OFFICE
CERTIFICATE OF CORRECTION

PATENT NO.        : 10,114,242 B2
APPLICATION NO.   : 15/162242
DATED             : October 30, 2018
INVENTOR(S)       : Kristina Magnusson Page 1 of 1

It is certified that error appears in the above-identified patent and that said Letters Patent is hereby corrected as shown below:

In the Specification

<u>Column 8</u>
Line 15, "polymide" should be corrected to read as -- polyimide --.
Line 18, "polymide" should be corrected to read as -- polyimide --.
Line 20, "polymide" should be corrected to read as -- polyimide --.

Signed and Sealed this
Twenty-second Day of January, 2019

Andrei Iancu
*Director of the United States Patent and Trademark Office*